(12) United States Patent
Devauchelle et al.

(10) Patent No.: US 8,454,701 B2
(45) Date of Patent: *Jun. 4, 2013

(54) SURGICAL METHOD FOR IMPLANTING A HOUSING-INTERFACE ASSEMBLY IN A BONE WALL

(75) Inventors: Bernard Devauchelle, Amiens (FR); Pierre Sabin, Paris (FR)

(73) Assignee: Plugmed Heart (FR)

( * ) Notice: Subject to any disclaimer, the term of this patent is extended or adjusted under 35 U.S.C. 154(b) by 604 days.

This patent is subject to a terminal disclaimer.

(21) Appl. No.: 12/631,176

(22) Filed: Dec. 4, 2009

(65) Prior Publication Data

US 2010/0145162 A1   Jun. 10, 2010

(30) Foreign Application Priority Data

Dec. 5, 2008 (FR) ..................... 08 58297

(51) Int. Cl.
*A61F 2/02* (2006.01)
(52) U.S. Cl.
USPC ...................................... 623/17.19
(58) Field of Classification Search
USPC ...................................... 623/17.19
See application file for complete search history.

(56) References Cited

U.S. PATENT DOCUMENTS

| 4,328,813 | A | 5/1982 | Ray |
| 4,495,917 | A | 1/1985 | Byers |
| 5,503,164 | A * | 4/1996 | Friedman ..................... 128/898 |
| 5,545,226 | A * | 8/1996 | Wingo et al. ............... 623/17.19 |
| 7,346,391 | B1 | 3/2008 | Osorio et al. |
| 8,083,782 | B2 * | 12/2011 | Ralph et al. ................... 606/283 |
| 2006/0224242 | A1 * | 10/2006 | Swords et al. ............. 623/17.19 |

FOREIGN PATENT DOCUMENTS

| DE | 4233605 C1 | 6/1994 |
| DE | 102005008454 A1 | 8/2006 |
| WO | 9732519 A1 | 9/1997 |
| WO | 2005065738 A2 | 7/2005 |
| WO | 2008054691 A2 | 5/2008 |

OTHER PUBLICATIONS

Search Report from Corresponding French Application 0858297 dated Jul. 7, 2009.

* cited by examiner

*Primary Examiner* — Bruce E Snow
*Assistant Examiner* — Melissa Hoban
(74) *Attorney, Agent, or Firm* — Lerner, David, Littenberg, Krumholz & Mentlik, LLP

(57) ABSTRACT

A surgical method for positioning an extraoral bone-anchored implant device in a receiving bone site of a patient, the patient being a human being or an animal, including the following successive steps: a step of preparing the receiving bone site, a step of impacting the implant in the opening formed in the receiving bone site; a step of leveling the implant and the surrounding bone structure and making them continuous, during which the external table of the bone structure is rubbed at its part surrounding the implant, then bone fragments are positioned on the rubbed parts of the external table of the bone structure, then the bone fragments are covered with a membrane to hold the bone fragments in position, the membrane being attached to the bone structure on one side and to the implant on the other side, so as to prevent bone proliferation on the implant.

8 Claims, 2 Drawing Sheets

SURGICAL METHOD FOR IMPLANTING A HOUSING-INTERFACE ASSEMBLY IN A BONE WALL

CROSS-REFERENCE TO RELATED APPLICATIONS

The present application claims the benefit of French Patent Application No. 0858297, filed Dec. 5, 2008, the disclosure of which is hereby incorporated herein by reference.

FIELD OF THE INVENTION

The present invention concerns the field of extraoral implantology applied to problems related to devices intended to enable an interaction between a human activity and a machine, i.e. human-machine interface devices such as brain-computer interfaces.

BACKGROUND OF THE INVENTION

Brain-computer interface devices (also called BCI devices) allow monitoring activity (electrical, thermal, or fluid, for example) in the human brain to directly control or transmit data to computers and associated electronic devices. There are two types of BCI devices: invasive or noninvasive. Noninvasive BCI devices are most often made up of electrodes placed on the patient's head to follow his or her cerebral activity. Although positioning of these devices was simple, the monitoring of cerebral activity was not optimal, primarily due to the distance separating the electrodes from the brain itself, and the obstacle created by the skin and sometimes the muscle, which can interfere with the signal quality. This is why invasive BCI devices have been developed, so that the activity can be measured closest to the areas of interest.

However, the development of electrical equipment to be installed inside the patient's body to alleviate a defect in a natural organ, such as for example brain-computer interfaces, as well as neuro-prostheses or even functional electrical stimulation, rely on the ability to transmit either the energy or the electrical signals required by this equipment from an energy or information source located outside the body toward the inside of the body, or for collecting information such as electrical signals originating from the defective natural organ and/or electrical equipment adapted to alleviate these defects.

The general objective of the present invention is therefore to offer a device that contributes to resolving the problems outlined above.

One aim of the present invention in particular is to propose a novel device permitting permanent integration of one or more interface devices as close as possible to the organs to be monitored and/or the corresponding electrical equipment implanted in the body.

Another aim of the present invention is to propose a device offering the possibility of housing an interface device serving as a relay and connecting the inside and the outside of a living organism.

Still another aim of the invention is to propose an innovative implantation method designed for the particular specific structure of the proposed bone-anchored housing-interface device.

SUMMARY OF THE INVENTION

For this purpose, an extraoral bone-anchored device and a corresponding housing assembly are proposed, such as defined in the attached claims.

More precisely, is proposed an extraoral bone-anchored implant device characterized in that it comprises an anchoring component with a outer lateral wall designed to cooperate with a bone structure provided with an opening in which the implant device is to be implanted, said outer lateral wall having a surface designed to ensure permanent anchoring of said implant device in the bone structure by osseointegration, said anchoring component further comprising an opening, said opening forming a cavity with a volume adapted to receive a housing device.

Some preferred but non-limiting aspects of the implant device, taken alone or in combination, are the following:
- the device comprises means for implantation through a through opening in the bone structure, and the anchoring component has a crown shape comprising a through opening, so that the cavity formed by said opening is open on both sides of the bone structure when the implant device is in position through said bone structure.
- the anchoring component is a crown having a cylindrical ring shape, the through opening being arranged along the axis of revolution of the cylindrical ring.
- the anchoring component is a crown having a truncated cone shape, the through opening being arranged along the axis of revolution of the truncated cone shape.
- the outer lateral wall has a rough surface to increase the osseointegration of the anchoring component with bone wall.
- the anchoring component has a shape and size adapted for an implantation through an opening within the cranial cavity.

A housing assembly is also proposed, to be implanted extraorally in a bone structure, characterized in that it comprises:
- the above bone-anchored implant device,
- a housing device comprising a body with an inner cavity, said body having an outer wall with a shape corresponding to the shape of the cavity formed by the opening of the implant device, and
- fixing means for fixing the housing device in the cavity of the implant device.

Some preferred but non-limiting aspects of this housing assembly, taken alone or in combination, are the following:
- the assembly further comprises sealing means arranged between the housing device and the implant device so as to prevent any fluid passage.
- the body of the housing device has an element forming a cap allowing access to the inner cavity of said body.
- the assembly further comprises an interface device comprising means for connection with one or more elements located inside the organism, said interface device being arranged in the inner cavity of the body of the housing device.
- the body of the housing device comprises electrical connection means suitable for electrical connection of the interface device with one or more organs and/or one or more electrical appliances located inside the organism.
- the body of the housing device comprises electrical connection means adapted for electrical connection of the interface device with one or more components and/or one or more electrical appliances located outside the organism.
- the interface device comprises an energy source to feed one or more electrical appliances located inside the organism.
- the interface device comprises means for controlling and/or monitoring one or more organs and/or one or more electrical devices located inside the organism.

the interface device comprises means for storing and/or processing data from one or more organs and/or one or more electrical devices located inside the organism.

the housing device comprises a body having a volume larger than the volume of the cavity formed by the opening of the anchoring component of the implant device.

A temporary implant assembly is also proposed, to be implanted extraorally in a bone structure, characterized in that it comprises:

the above bone-anchored implant device, a closing device for closing the opening of the anchoring component of the implant device, said closing device comprising a solid body with an outer wall having a shape corresponding to the shape of the cavity formed by the opening of the implant device, and fixing means for fixing the closing device in the cavity of the implant device.

This temporary implant assembly may further comprise a fastener coupled to the implant device and/or the closing device to keep a membrane in position against an upper wall of the implant device.

Finally, is proposed a surgical method for positioning an extraoral bone-anchored implant device in a receiving bone site of a patient, said patient being a human being or an animal, comprising the following successive steps:

step of preparing the receiving bone site, during which:
  the cutaneous plane facing the receiving bone site is incised, then
  the periosteum of the receiving bone site is first detached and then reclined to clear the bone structure, then
  the bone structure is cut in order to create an opening in which the implant device will be positioned;

step of impacting the implant in the opening formed in the receiving bone site;

step of leveling the implant and the surrounding bone structure and making them continuous, during which:
  the external table of the bone structure is rubbed at its part surrounding the implant, then
  bone fragments are positioned on the rubbed parts of the external table of the bone structure, then
  said bone fragments are covered with a membrane to hold the bone fragments in position, said membrane being attached to the bone structure on one side and to the implant on the other side, so as to prevent bone proliferation on said implant.

Some preferred but non-limiting aspects of this surgical method, taken alone or in combination, are the following:

during the step of preparing the receiving bone site, a collecting filter positioned on a suction device is used for collecting the bone fragments resulting from cutting of the bone structure, in order to use said bone fragments during the step of leveling.

the step of preparing the receiving bone site is done under continuous irrigation to limit heating of the receiving bone site.

after the opening is formed in the bone structure, the edges of the opening are shaped with a rotary instrument for forming an opening with a truncated cone shape.

the step of impacting the implant comprises first the insertion of the implant device, then progressive impaction of said device in the opening by tapping the implant to force it into the opening.

the implant is impacted by using a tool provided with at least a drift-punch element inserted into a groove provided on the upper surface of the implant, and then tapping on the tool to force the implant into the opening.

the surgical method further comprises a step of bone integration consisting of covering the membrane and the flush portion of the implant by the periosteum and then by the skin flap of the patient, after a hematoma drain has been positioned.

the surgical method comprises a second surgical phase of 3 to 4 months after the first phase for impacting the bone-anchored extraoral implant, said second surgical phase comprising a step of positioning a housing device in an opening provided in the implant device, in replacing a temporary closing device that was positioned in said opening during the first surgical phase.

at least one interface device is positioned in the housing device, said interface device being then connected to one or more elements situated inside the organism of the patient.

the interface device is further connected with devices for transmission with the outside of the organism of the patient, said transmission devices being positioned in the organism of the patient subcutaneously or percutaneously.

BRIEF DESCRIPTION OF THE DRAWINGS

Other characteristics and advantages of the invention will appear from the following description, which is purely illustrative and non-limiting and should be read with regard to the attached drawings, in which.

DETAILED DESCRIPTION OF THE INVENTION

Extraoral Bone-Anchored Implant Device Forming Housing-Interface

The principle of the present invention is to implant a housing extraorally inside the body of a patient, said patient being an animal or a human being, as close as possible to an organ that one seeks to monitor. For this purpose, is proposed the use of a housing to be encased in a bone structure serving as a bone substrate and situated near said organ.

More precisely, the housing that is proposed has a particular structure allowing it to be integrated into a bone structure serving as the bone substrate, i.e. osseointegrated in the meaning of the expression used in implantology, which has several advantages compared to other types of fixation, such as will be seen later on in the text. By osseointegration, one thus refers to a bone proliferation (generally an osteoblastic proliferation) directly on the walls of the implant device (generally provided with Titanium or Zirconia) with no interposition of fibrous tissue, which thus guarantees a perfect sealing of the fixation.

Once such a housing has been effectively integrated into the bone structure near the organ to be monitored, this housing will permit inserting an interface device comprising any supply and/or surveillance system and electrical, electronic or computerized regulation of said organ, or an internal electrical appliance (including any electronic or computer appliance) located inside the human (or animal) body and connected to this organ. The assembly formed makes up a bone-anchored housing-interface (BAHI, or BIIO standing for the French expression "Boitier-interface intra-osseux").

By the expression "monitoring an organ", one refer to any operation seeking to measure, oversee, record, analyze, etc. the activity of an organ, as well as any operation seeking to act on said organ, for example in view of a particular therapy.

In the particular case of bone-computer interface devices, the main objective of the proposed device is to position a housing in the cranial cavity bone with an outer face situated under the scalp and an inner face facing the meninx.

Thus, it is possible to position connection means at the inner face opposite the organ to be monitored that allow connection, particularly electrical connection, with said organ or with one or more electrical appliances located next to the organ, to monitor it and send or receive signals or electrical energy. The outer face of said device is preferably connected to the outside of the body by means of suitable connections, such as a permanent percutaneous electrical connection (PPEC, or CEPP standing for the French expression "Connexion électrique percutanée permanente"), a transcutaneous electrical connection (TCEC, or CETC standing for the French expression "Connexion électrique transcutanée") or any other system for connecting the outer face with the outside of the body.

According to this configuration, an interface device is positioned inside the housing cavity that is to be connected with the inside of the body (that is inside of the organism of the patient), to an electrical appliance situated near the organ or directly to said organ, via a connection means associated with its inner face.

When necessary, the interface device can also be connected with the outside of the body (that is outside of the organism of the patient), possibly by means of the outer face of the housing and the associated connection means.

The interface device positioned inside the housing cavity can comprise an energy source for the electrical appliances positioned inside the body, a system for surveillance and/or electrical, electronic, or computerized regulation of the electrical appliances inside the body or the organs, as well as means for processing data coming from said electrical appliances or organs, and means for storing these data.

Figure 1:
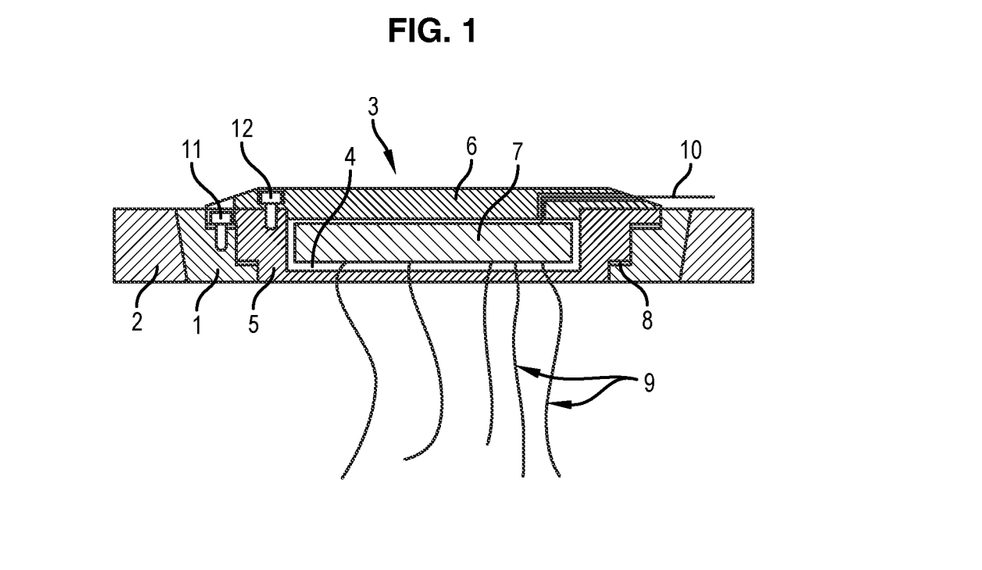
FIG. 1 is a schematic illustration, in sectional view, of the housing-interface assembly according to the invention to be implanted in a bone substrate.

The main element making up the housing assembly to be implanted through a bone wall near the organ to be monitored resides in a particular extraoral bone-anchored implant device, which is designed on the one hand to be impacted and osseointegrated into a bone wall 2, and on the other hand to possibly allow a communication between elements located on either side of bone wall 2.

For this purpose, is proposed using an implant device that has an anchoring component 1 whose outer wall is designed to cooperate with bone wall 2 through which said implant device is to be implanted. Proposed implant device is an extraoral implant, i.e. adapted to be implanted extraorally, and is thus not a dental implant. It can nevertheless have points in common, notably with regard to the material of which it is made, the surface state of the part of the implant in contact with the bone and the overall implantation method, in two procedures: integration of the implant and then activation of this implant.

Anchoring component 1 further comprises an opening designed to form a cavity with a sufficiently large volume to receive a device forming a housing, i.e. a device comprising an inner cavity inside which an interface device such as outlined above can be positioned. Preferably, this opening passes through completely, i.e. the cavity formed by such through opening connects both sides of the bone wall when the implant is in position, through an opening also crossing through the bone wall (this opening can be pre-existing or especially created for this implantation). Thus, the through opening forms a passage open on both sides of the bone wall. For some particular bone sites such as the iliac wings, the opening made in the bone wall may be a blind hole, so that the opening made in anchoring component 1 of the implant device does not need to be a through opening.

Anchoring component 1 can have any form with the characteristics described above. For example, a crown-shaped anchoring component 1 can be used, in particular a crown in the form of a cylindrical ring whose through opening is made along the axis of revolution of said ring. Anchoring component 1 may also be a crown having a truncated cone shape whose through opening is also created along the axis of revolution of the truncated cone shape. The outer inclined walls of such an anchoring component allow insertion and better cooperation of anchoring component 1 with bone wall 2. For an anchoring component 1 with these particular forms, the walls designed to cooperate with bone wall 2 correspond to lateral walls.

The walls designed to cooperate with bone wall 2 have a surface designed to promote impaction of anchoring component 1 in said bone wall 2 and also to promote the osseointegration of anchoring component 1 in bone wall 2. Thus, for example, an outer surface can be provided having a certain roughness, in particular for increasing the contact surface between the anchoring component 1 and the bone wall 2, and thus promoting primary stabilization and then osseointegration of the anchoring component 1 in the bone wall 2, which can be related to a "weld" between these two elements. Preferably, the anchoring component is made of titanium, possibly with a treated outer surface, further promoting bone integration of the device. For example, the treatment may consist of a bombardment of the lateral anchoring walls with titanium dioxide or with silica grain, which deforms these walls and promotes osseointegration. The walls may also be acid etched.

Also, one or more grooves can be provided on the upper surface of the crown (i.e. the surface of the crown on the side of the skin), these grooves serving as a guide when the crown is positioned in the receiving bone. Preferably, a circular groove is made on the upper surface of the crown.

Given the volume necessary for incorporating one or more interface devices 7 inside the cavity of the housing device 3, which we will discuss in more detail below, anchoring device 1 is preferably inserted through an opening made beforehand in corresponding bone wall 2. Thus, the outer walls of said anchoring component 1 are not necessarily threaded for the insertion of said anchoring component into bone wall 2.

The housing-interface assembly also comprises a device forming housing 3 that is to be positioned inside the cavity formed by the through opening created inside the body of anchoring component 1.

This housing device 3 is formed so as to have an inner cavity 4 to receive one or more interface devices 7. When the housing device has a roughly cylindrical shape, it can for example have a cavity volume close to 20 $cm^3$, for a housing of 5 cm diameter and 1 cm height. The size of the housing device may however vary depending of the volume of the interface devices to be housed.

Housing device 3 has a suitable shape so that its outer walls conform perfectly to the inner walls of anchoring device 1, i.e. it fits perfectly inside the cavity formed by the through opening of implant device 1 and the corresponding walls are as close as possible to one another.

Preferably, the inner walls of anchoring component 1 and the outer walls of housing device 3 have a shape promoting cooperation and holding the two devices in one another. In particular, these inner and outer walls can be inclined with regard to the axis of revolution of said implant device and housing device 3. These walls can also have parts forming a stop for better assembly of housing device 3 in implant device.

Preferably, a gasket 8 is fitted between the inner and outer walls of housing device 3 and implant device respectively, for sealing purposes. This gasket 8 is designed to prevent any flow of fluid through the assembly formed by implant device and housing device 3, so that the bone wall integrating the bone-anchored implant assembly has a seal similar to the seal existing before integration of said assembly. Preferably, a toric gasket is positioned against the inner wall of the crown of the implant device. A groove may be etched on the inner wall for easing the positioning of the toric gasket.

Finally, fixing means 11 are provided to affix the housing device 3 in the cavity of the implant device, by a screw system, for example, such as locking cams reversible by rotating the head.

The housing device 3 preferably has a volume roughly equal to the volume of the cavity formed by the opening created in the anchoring device 1. This allows a better integration of the housing-interface assembly. However, according to another embodiment, the housing device 3 has a volume slightly larger than the volume of the cavity formed by the opening made in the anchoring component 1, which permits having an inner cavity 4 for receiving the interface device with a larger volume. In the case of integrating the housing-interface assembly through the cranial cavity, the body forming the housing device 3 can, for example, extend slightly beyond the anchoring component 1, in the space between the brain and the inner table of the cranial bone site where the device will be impacted.

Body 5 forming housing 3 has a component 6 forming a cap or cover allowing access to inner cavity 4 created inside housing device 3. This component 6 forming a cap also allows inserting interface device 7 in the housing device 3 if desired, for example, before affixing the housing device 3 in the implant device 1. Fastening means 12 are also provided so that component 6 forming the cover can be hermetically sealed, preventing any infiltration inside inner cavity 4.

Moreover, the housing device 3 has electrical connection means 9 designed for an electrical connection of interface device 7 with one or more electrical appliances located inside the body, and/or directly with one or more organs. These connection means 9 will, for example, have the form of flexible wires connected to the organs by means of electrodes, or directly connected to electrical devices or appliances positioned near the organs to be monitored. Furthermore, any other connection means 9 can be provided, including wireless, particularly allowing data exchange. These connection means 9 are positioned on the inner face of housing device 3, i.e. the surface facing the organs to be monitored.

On the outer face of housing device 3, i.e. the face next to the outer table side of the cranial bone site where the device is impacted, connection means 10 can be provided with one or more electrical appliances located outside the body. Thus, for example, it will be possible to connect an interface device 7 positioned in cavity 4 of the housing device 3 to a permanent percutaneous electrical connection (PPEC or CEPP) emerging on the outside of the body, or a transcutaneous electrical connection (TCEC or CETC) (having the advantage of not emerging on the outside of the body), by means of which it will be possible to connect interface device 7 positioned inside the body with the outside. Obviously, any other means for transferring electricity from one side of the skin to the other may also be used for this purpose.

This particular configuration of housing device 3 allows integrating the inside of inner cavity 4 with one or more interface devices 7 serving as a relay to connect the inside and outside of the body for therapeutic purposes or any other purpose.

Interface device 7 can, for example, comprise an energy source feeding one or more electrical appliances positioned near the organs to be monitored. Such an energy source can, for example, be a battery that can be recharged by means of connection means 10 set up toward the outside of the body.

The interface device can also comprise any other device permitting monitoring electrical appliances located inside the body, or directly monitoring the organ or organs of interest. Thus, interface device 7 can, for example, comprise surveillance means and electrical, electronic, or computerized regulation means for the organ or organs or electrical appliances inside the body. Interface device 7 can also comprise means for storing data coming from electrical appliances located inside the body, even means for processing data coming from these appliances.

Connection means 10 to be connected with the outside of the body allow data exchange from the inside of the body to the outside of the body, and vice versa.

Figure 2:
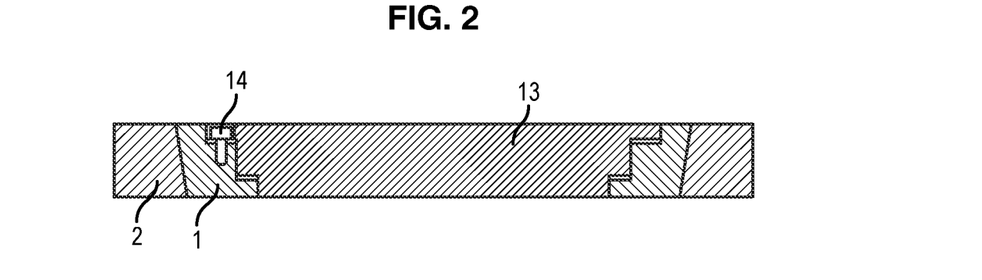
FIG. 2 is a schematic illustration, in sectional view, of the temporary implant assembly to be implanted in a bone structure.

As will be seen later in the procedure for positioning the bone-anchored housing-interface assembly, there is a healing phase necessary for permanent integration of implant device 1 in bone wall 2, in which a closing device 13 is used temporarily for closing the through opening made in the body of implant device.

This closing device 13 comprises a solid body whose outer wall is identical to the outer wall of body 5 of housing device 3, so that this closing device perfectly conforms to the shape of the inner wall of the cavity formed by the through opening of implant device.

This temporary closing device 13 is affixed onto implant device by appropriate means 14, such as, for example, a locking cam reversible by rotating the head.

Furthermore, a fastener (not shown) can also be provided, coupled to temporary closing device 13 (for example screwed onto it) and designed to hold a membrane in place promoting bone proliferation between bone wall 2 and crown. This fastener is further designed to prevent the bone from proliferating above the upper wall of crown. According to a preferred embodiment, this fastener is present in the form of a plate, for example ring shaped, that presses the membrane against the upper wall of the crown.

As has already been specified, the fact that the bone-anchored housing-interface is permanently affixed to the bone substrate by osseointegration is particularly advantageous, particularly compared to existing devices provided with other fixation means. These advantages can be listed according to several analytical angles:

From the viewpoint of longevity of the installation in situ: osseointegrated implants are provided so as to remain in place permanently, anchored in the bone structure, while fixations using osteosynthesis screws are used for temporary fixation of elements in the bone wall, or to temporarily hold bone parts together.

From the viewpoint of seal: the quality of the barrier established by bone proliferation in contact with a titanium surface previously treated to increase the bone-implant contact surface is incomparably better than a metal part positioned on or in a bone that leaves spaces between the bone wall and said metal part.

From the viewpoint of patient comfort and safety, affixing the bone-anchored housing-interface by osseointegration prevents the housing from projecting above the surface of the anchoring bone structure, which is particularly not the case for devices of the prior art anchored by using osteosynthetic screws.

From the viewpoint of accessibility: the bone-anchored housing-interface designed in two parts, i.e. the osseointegrated crown (true extraoral implant) and the housing itself which is positioned in this crown in place of a temporary plate, allows simple installation of electrical, electronic, or computerized connections at a later point in time. In fact, it is useful to separate the surgical procedure for implanting the equipment designed to remain in place for years and the installation of equipment (electrical, electronic, or computerized) that must be housed in the housing. Osseointegration thus ensures that the bone-anchored housing-interface is installed properly before positioning the monitoring devices (onerous) contained in the housing, which represents a certain advantage. Moreover, the housing is designed to be easily detached from the crown, allowing rapid and simple change of the housing as well as the equipment positioned at the organ. Thus, in the case of application to the brain, this equipment and methodological design is called "Brain Direct Access".

Surgical Implantation Method

The surgical method described below relates to the installation of a bone-anchored housing-interface apparatus designed to reside permanently in a receiving bone site, possibly for the entire lifetime of the patient in whom it is positioned, whether this patient is a human being or an animal.

The principle of the invention is to propose a bone-anchored housing-interface with a structure allowing it to be truly integrated in the receiving bone structure, i.e. osseointegrated, following an innovative implantation method designed for this particular specific structure.

Figure 3:
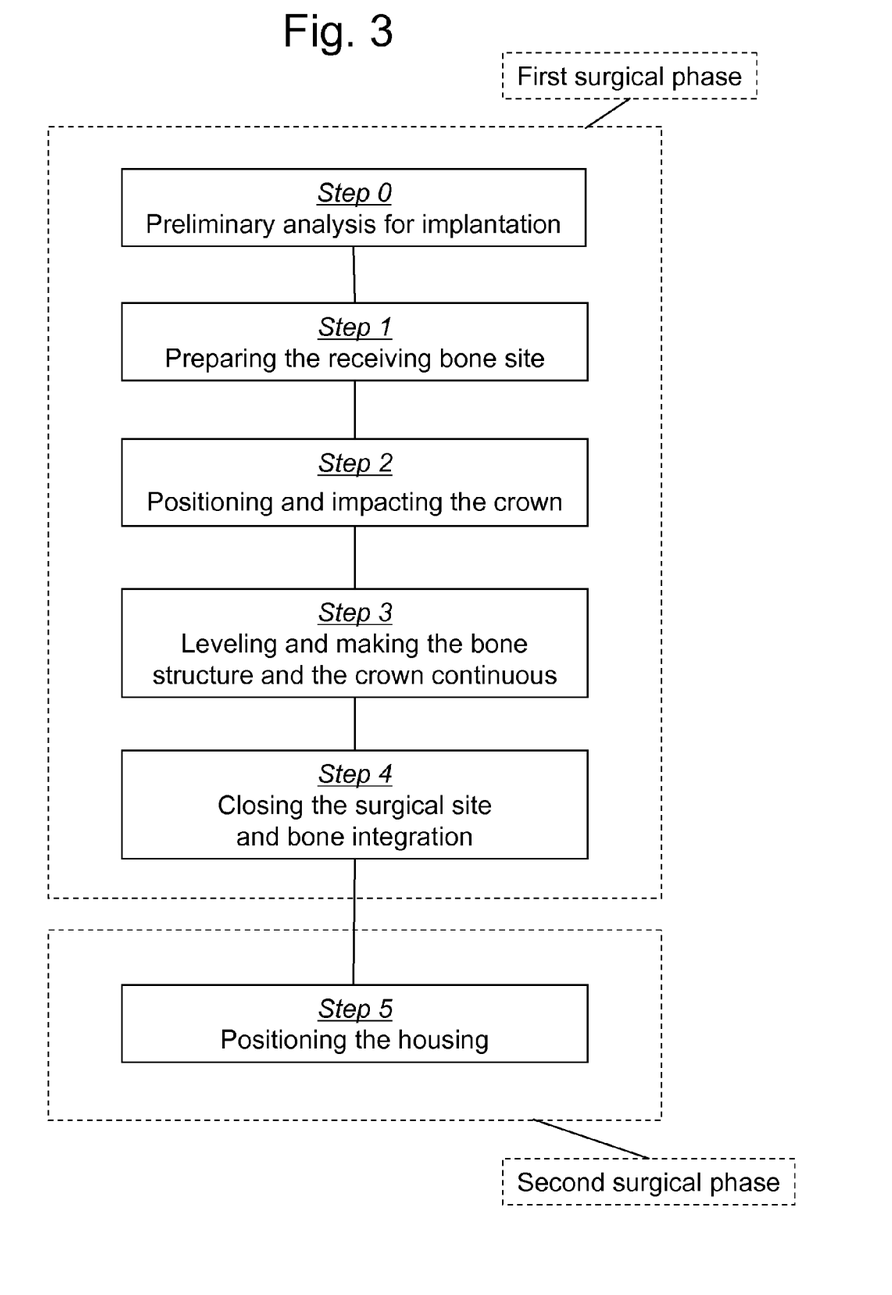
FIG. 3 is a schematic illustration of the surgical method for implantation of the extraoral bone-anchored implant device according to an embodiment of the invention.

The procedure for positioning the bone-anchored housing-interface assembly described above takes place in two main steps, i.e. a step of integration of implant device 1 and corresponding healing allowing implant device 1 to be affixed by osseointegration, and a step of final positioning of the housing device 3 enclosing interface device 7.

Therefore the first step consists of inserting the body of the implant device 1 in an opening created inside bone wall 2 so that the outer face of anchoring component 1 is in contact with the bone site in which the implant device 1 will be impacted.

During this integration phase of the implant device 1 in bone wall 2, said implant device 1 is associated with closing means 13 presented above, which is temporarily positioned in the cavity formed by the through opening made in anchoring component 1, so as to perfectly block off the passage open on both sides of the bone wall.

The osseointegration of implant device 1 is also improved by promoting bone growth on the outer bone table, so that the outer bone table can be level and continuous with the upper surface of the implant device. This step consists of covering a rubbed part of the bone surface of the outer table with bone fragments and a healing membrane.

The permanent integration of implant device 1 with the bone wall requires a period of three to four months for strengthening the bonds between the outer wall of the anchoring component 1 and corresponding bone wall 2 so that the implant device 1 is correctly integrated in bone wall 2.

Once this phase of prior integration of device 1 is properly completed, i.e. when implant 1 is fully osseointegrated in corresponding bone wall 2, temporary closing device 13 should be replaced with housing 3 integrating interface 7 configured according to the organ monitoring needs.

Once the housing device 3 is positioned, the housing-interface assembly implanted in the bone wall as described above forms an interface, particularly an electrical interface, between the inside and the outside of the body since interface device 7 can be connected on one side to the outside of the body via a permanent percutaneous electrical connection (PPEC or CEPP), a transcutaneous electrical connection (TCEC or CETC), or any other means allowing electricity (or any other signal, like a radiofrequency signal) to pass through the skin, and can be connected on the other side with the organs and appliances implanted in the body.

The surgical protocol for installing a bone-anchored housing-interface is governed by two types of rules; some are common to all receiving bone sites, and others are particular to each anatomical type of receiving bone site (cranial bone, iliac wing, sternum, etc.).

For the principal description of the protocol for positioning a bone-anchored housing-interface (BAHI or BIIO) assembly, we will use the cranial position, particularly in the parietotemporal region, the preferred location for applications directly or indirectly concerning the brain. Surgical rules specifically relating to positioning a bone-anchored housing-interface (BAHI or BIIO) cranially essentially concern the approach and then the positioning of the anchoring component of the implant device, this anchoring component being crown-shaped, preferably as a truncated cone, and then causing the bone to be leveled around the impacted crown.

Step 0 (Optional): Preliminary Analysis for Implantation

An optional but preferred first step consists of examining the receiving bone site by imaging (scanning and/or x-ray), by a virtual simulated implantation, and then possibly by simulated implantation by means of a stereolithographic cranial model corresponding to the receiving bone site.

Step 1: Preparing the Receiving Bone Site

The surgical procedure for positioning a bone-anchored housing-interface must follow the rules common to all bone sites receiving an extraoral implant. In particular, the bone site must be approached while respecting the surrounding soft tissue, while limiting bleeding (for example hemostasis by electrocoagulation), and while sufficiently clearing the receiving bone site so as to be able to use the ancillary equipment without injuring the adjacent soft tissue.

The approach can be bicoronal, by U flap, or by zigzag or straight incision in reverse arrow.

Once the periosteum is incised, detached and reclined (by reclined is meant bent or curved downward and/or backward), the cranial bone can be cut with a crown trepan or any other means allowing cutting part of the cranial vault involving both the inner and outer tables.

The receiving bone site is prepared, i.e. the opening designed to receive the implant is formed by cutting the bone site, making sure that the temperature due to friction from the rotary instruments on the bone does not lead to an inflammatory reaction that will impede osteoblast proliferation. In fact, regeneration of the receiving site bone is linked to osteoblast proliferation, and this is incompatible with a large increase in bone temperature. This bone temperature elevation is limited by abundant irrigation with slightly cooled serum during the phases of cutting or planing the receiving bone site. Thus, in order to allow the receiving bone site to regenerate in the form of neoformed bone by osteoblast stimulation, it is preferable to prepare the receiving bone site while keeping the temperature due to rotary instrument friction on the bone from exceeding 43° C.

Done with continuous irrigation, this first phase of the protocol allows collecting the bone fragments by means of a collecting filter positioned on a suction device.

Continually checking the progress of cutting through the cranial bone shows that at a certain depth of the crown trepan, the inner table is on the point of being overshot in places, the crown saw being graduated and the bone thickness known from preoperative imaging (scanning and stereolithographic reconstruction).

The final cutting makes use of piezosurgical cutting in order to avoid injuring underlying soft tissue.

Once the bone round piece has been removed, the edges of the opening are shaped with a rotary instrument to create a truncated cone shaped opening.

The receiving site preparation is checked by means of the bone-anchored housing-interface crown or by a model of this crown, so that the receiving site truly has a shape complementary to the crown.

Step 2: Positioning and Impacting the Crown

The crown is positioned according to the following impaction protocol: the crown (generally attached to the temporary closing plate) is set up in front of the opening made in the cranial vault. Since the crown has a similar shape, however with a slightly greater diameter, to the instrument that makes the final truncated cone, it is adjusted approximately to the opening made with the crown trepan.

The slightly truncated crown, according to a cone that can range from 0 to 89°, and ideally of the jaw type, is presented in front of the opening made in the cranial vault according to its smaller diameter, which is designed to be located at the deepest part of the opening made in the bone structure. Thus, the crown can be approximately inserted in the opening, penetrating into it by several millimeters.

The crown is then very gently impacted, the rough and irregular surface of its walls being in contact with the edges of the bone opening, conforming to the stereolithographic model created. The wall of the crown is progressively inlaid in the bone opening as it is inserted.

Impaction requires gentle taps around the circumference of the crown in order to progressively impact the crown for it to take its position along an axis ideally superposing the axis of the opening.

In order to avoid damaging the machined inner part forming the opening that will receive the housing-interface device, this part is protected by the temporary closing plate totally covering the machined face and partially covering the crown surface corresponding to the widest base of the truncated cone represented by the crown. One or more parallel grooves made on the side of the machined part of the crown serve as a guide for the instrument receiving the taps with the hammer. Such grooves are therefore not covered by the edges of the temporary plate.

Step 3: Leveling and Making the Bone Structure and the Crown Continuous

Once positioned conforming to the information provided by the stereolithographic model, the bone around the crown should be impacted so that the metal edge of the impacted implant does not damage the skin flap that will cover the bone-anchored housing-interface assembly. In order to obtain leveling and continuity between the outer bone table surface and the crown surface (and the temporary plate) the bone is thickened. To this end, is preferably used the bone fragments from the patient, gathered during the step of preparing the receiving bone site. One may also use a bone substitute component.

To do this, the bone surface of the outer table surrounding the impacted crown is rubbed with an abrasive instrument, ideally rotary, like a bone drilling bur, in order to make these parts of the bone bleed. Thus, the bone surface is rubbed so as to get a bared bleeding surface. Then the bone fragments collected during bone cutting are positioned on this rubbed part of the bone, taking care that these bone fragments do not go above the upper surface of the crown and the temporary plate. The bone is rubbed and therefore slightly hemorrhagic so that the (collected) bone fragments placed in contact form an onlay graft.

The bone fragments are positioned so as to make the bone level around the crown so that the metal of the crown is flush with the bone substrate in a harmonious manner.

The use of a biocompatible membrane (resorbent or non-resorbent) may prove useful or even necessary for this leveling.

In fact, in order for the bone fragments not to disperse, they are preferably covered with a resorbent or non-resorbent membrane, cut out at the temporary plate. This membrane covers the bone fragments so as to even out the bone plane around the crown and hold these bone fragments against the rubbed bone wall to promote bone proliferation.

This membrane is held on the bone structure by any fixation means, such as osteosynthetic screws positioned around its periphery. The membrane is also affixed to the implant, held, for example, by a piece screwed onto the temporary plate so as to hold the membrane tight against the crown in order to prevent the bone from proliferating in this area.

Preferably, the membrane used is made in PTFE (polytetrafluoroethylene), a non-resorbent material that particularly promotes bone proliferation.

Step 4: Closing the Surgical Site and Bone Integration

The membrane and the crown with its temporary closing plate are next covered by the periosteum, then the skin flap, which is closed after a hematoma drain has been installed, for example a redon or filiform drain.

The crown can therefore be progressively integrated into the bone wall during a variable duration, from three to four months for example, as a function of the bone structure.

This first phase, called "mise en nourrice" in French, allowing the implant to be correctly integrated in the bone wall, has a duration of three to four months according to the type of bone of the receiving site, which can vary from bone that is not very mineralized to bone that is extremely mineralized.

Step 5: Positioning the Housing

Finally, in a second surgical phase, after the several months necessary for bone integration, the temporary plate is removed in order to be replaced by the housing-interface device itself.

To do this, the skin is cut again and pulled back. The periosteum is again widely cut so as to remove the bone proliferation membrane, in particular if this later is non-resorbent. Fixation means used at the periphery of the membrane to affix it to the bone structure are also removed, except if they were resorbent screws. Using resorbent screws may be advantageous as it enables having a smaller incision during this second surgical phase.

If necessary, the excess bone that has proliferated under the membrane, toward the crown is removed.

The temporary plate is then unscrewed and removed so as to allow permanent positioning of the housing.

The connections to the devices positioned inside the cranial cavity as well as the couplings with the transmission means (subcutaneous or percutaneous) with the outside of the human (or animal) body are made at this stage. This involves a close collaboration with the neurosurgical team.

Once the couplings are made and the device is permanently positioned, the periosteum can be returned to position and the skin flap can be closed.

As has been stated above, the extraoral bone-anchored housing-interface assembly is particularly advantageous with regard to brain-computer interface devices. In this case, the housing-interface implant assembly is integrated through the bone wall of the cranial cavity.

However, the assembly can also be integrated into a bone site other than the cranium, such as, for example, the iliac wing or the sternum. In this case, coupling with a permanent percutaneous electrical connection (PPEC or CEPP), a transcutaneous electrical connection (TCEC or CETC), or any other means allowing electricity to pass through the skin can still be done at the cranium where the positioning means are more precise than for the rest of the anatomy.

Furthermore, the extraoral bone-anchored housing-interface assembly presented has advantages related to the implantation technique used, which comprises the principal steps of osseointegration protocols that have been adapted or supplemented to correspond to the characteristics of the device as much as possible. The classical osseointegration protocol corresponds to a precise protocol that does not allow for any improvisation in its application; consequently the results are predictable and reproducible and thus "non-operator dependent", except in the case of medical accidents.

The specific implantation method proposed also relies on a precise protocol that does not leave any room for improvisation. Furthermore, the equipment used is of simple design, although very specific. As a result of this, the extraoral bone-anchored housing-interface osseointegration is a simple and reliable surgical procedure well within the competence of maxillofacial surgeons, neurosurgeons and ENT specialists.
Description of the Specific Equipment Used for Positioning the Bone-Anchored Extraoral Housing-Interface Any operation for positioning an extraoral bone-anchored housing-interface is preferably preceded by imaging the receiving site: teleradiographs, particularly face and profile, and especially scanning and equipment pre-positioning software. Possibly, an anatomical reconstruction by stereolithography will allow visualizing the proper positioning of the bone-anchored extraoral housing-interface with a template.

Various means, manual or mechanical, can be used to prepare the receiving bone site: cutting out a segment of the cranial vault with a conventional neurosurgery saw or a fissure bur with depression guard. This cutout can also be made by means of a piezosurgical hand piece.

More simply, an instrument of the crown trepan type can be envisioned, with a center-finding drill allowing precise, rapid, and possibly "robot-controlled" cutting, i.e., an automated mechanical means.

The final preparation of the edge of the opening is done with a truncated cone bur instrument with an irrigation and suction system to prevent bone fragments from getting inside the cranial cavity, and possibly a system for collecting these bone fragments.

The crown can be impacted into the opening created by the crown trepan by tapping lightly on the crown by means of a drift punch instrument whose end will be lodged in the groove, preferably circular, located on the external upper face of the crown. This avoids tapping directly on the crown with a hammer (Lombard hammer). Marked tapping areas made up of specific markings (for example numbers) etched in the groove, allow alternately tapping on these various areas, evenly impacting the crown. A more specific tool can also be used, comprising as much drift punches as impact markings etched in the groove of the crown, these punches being connected together by a common tapping element on which the surgeon can tap to apply an equal insertion force to each impact area.

The reader will understand that various modifications can be introduced without exceeding the scope of the novel disclosures and advantages described here. Consequently, any modifications of this type are incorporated in the bone-anchored device, the implant housing assembly and the temporary implant assembly according to the invention.

The invention claimed is:

1. A surgical method for positioning an extraoral bone-anchored implant device in a receiving bone site of a patient, said patient being a human being or an animal, comprising a first surgical step comprising the following successive steps:
   step of preparing the receiving bone site, during which:
      the cutaneous plane facing the receiving bone site is incised, then
      the periosteum of the receiving bone site is first detached and then reclined to clear a bone structure, then
      the bone structure in the receiving bone site is cut in order to create an opening in which the implant device will be positioned;
   step of impacting the implant in the opening formed in the receiving bone site;
   step of leveling the implant and the surrounding bone structure and making them continuous, during which:
      an external table of the bone structure is rubbed at its part surrounding the implant, then
      bone fragments are positioned on the rubbed parts of the external table of the bone structure, then
      said bone fragments are covered with a membrane to hold the bone fragments in position, said membrane being attached to the bone structure on one side and to the implant on the other side, so as to prevent bone proliferation on said implant;
wherein the method comprises a second surgical phase of 3 to 4 months after the first surgical step for impacting the bone-anchored extraoral implant, said second surgical phase comprising a step of positioning a housing device in an opening provided in the implant device, in replacing a temporary closing device that was positioned in said opening during the first surgical step.

2. The surgical method of claim 1, wherein, during the step of preparing the receiving bone site, bone fragments resulting from cutting of the bone structure are collected, in order to use said bone fragments during the step of leveling.

3. The surgical method of claim 1, wherein the step of preparing the receiving bone site is done under continuous irrigation to limit heating of the receiving bone site.

4. The surgical method of claim 1, wherein, after the opening is formed in the bone structure, the edges of the opening are formed with a truncated cone shape.

5. The surgical method of claim 1, wherein the step of impacting the implant comprises first the insertion of the implant device, then progressive impaction of said device in the opening by tapping the implant to force it into the opening.

6. The surgical method of claim 1, further comprising a step of bone integration consisting of covering the membrane and flush portion of the implant by the periosteum and then by skin flap of the patient, after a hematoma drain has been positioned.

7. The surgical method of claim 1, wherein at least one interface device is positioned in the housing device, said interface device being then connected to one or more elements situated inside an organism of the patient.

8. The method of claim 7, wherein the interface device is further connected with devices for transmission with the outside of the organism of the patient, said transmission devices being positioned in the organism of the patient subcutaneously or percutaneously.

* * * * *

UNITED STATES PATENT AND TRADEMARK OFFICE
CERTIFICATE OF CORRECTION

PATENT NO. : 8,454,701 B2
APPLICATION NO. : 12/631176
DATED : June 4, 2013
INVENTOR(S) : Bernard Devauchelle et al.

It is certified that error appears in the above-identified patent and that said Letters Patent is hereby corrected as shown below:

In The Claims

Column 14, line 61, "and flush" should read --and a flush--

Signed and Sealed this
Nineteenth Day of April, 2016

Michelle K. Lee
*Director of the United States Patent and Trademark Office*